United States Patent
Groiselle et al.

(10) Patent No.: US 8,492,723 B2
(45) Date of Patent: Jul. 23, 2013

(54) METHOD OF ANALYSIS OF AN OBJECT BY NEUTRON INTERROGATION, BY THE ASSOCIATED PARTICLE TECHNIQUE, AND DEVICE FOR IMPLEMENTING THE METHOD

(75) Inventors: Corinne Groiselle, Crosne (FR); Jean-Luc Dumont, Limeil-Brevannes (FR); Philippe Le Tourneur, Ozoir la Ferriere (FR)

(73) Assignee: Societe Anonyme d'Etudes et Realisations Nucleaires, Limeil-Brevannes (FR)

( * ) Notice: Subject to any disclaimer, the term of this patent is extended or adjusted under 35 U.S.C. 154(b) by 505 days.

(21) Appl. No.: 12/774,952

(22) Filed: May 6, 2010

(65) Prior Publication Data

US 2010/0288932 A1 Nov. 18, 2010

Related U.S. Application Data

(60) Provisional application No. 61/289,793, filed on Dec. 23, 2009.

(30) Foreign Application Priority Data

May 13, 2009 (FR) ..................................... 09 53169

(51) Int. Cl.
*G01F 23/00* (2006.01)
(52) U.S. Cl.
USPC ........................................................ 250/358.1
(58) Field of Classification Search
USPC .................... 250/358.1, 390.01–390.12, 391
See application file for complete search history.

(56) References Cited

U.S. PATENT DOCUMENTS

| | | | | |
|---|---|---|---|---|
| 4,593,195 A * | 6/1986 | Bienfait et al. | ............... | 250/253 |
| 5,557,108 A * | 9/1996 | Tumer | ...................... | 250/390.04 |
| 6,297,507 B1 * | 10/2001 | Chen et al. | ............... | 250/370.11 |
| 7,026,944 B2 * | 4/2006 | Alioto et al. | .................. | 340/600 |
| 7,420,175 B2 * | 9/2008 | Chu et al. | ................... | 250/358.1 |
| 2003/0165213 A1 * | 9/2003 | Maglich | ........................ | 376/159 |
| 2005/0195931 A1 | 9/2005 | Maglich | | |
| 2006/0098773 A1 * | 5/2006 | Peschmann | ..................... | 378/57 |

FOREIGN PATENT DOCUMENTS

FR 2 738 669 A1 3/1997
WO WO 2004/064462 A1 7/2004

OTHER PUBLICATIONS

U.S. Appl. No. 12/772,509, filed May 3, 2010, Le Tourneur.
U.S. Appl. No. 12/773,416, filed May 4, 2010, Le Tourneur.
E. Rhodes, et al., "APSTNG: Radiation Interrogation for Verification of Chemical and Nuclear Weapons", Proceedings of the Nuclear Science Symposium and Medical Imaging Conference, XP-010058037, Nov. 2, 1991, pp. 1293-1297.
D. L. Chichester, et al., "The API 120: A portable neutron generator for the associated particle technique", Nuclear Instruments and Methods in Physics Research B, vol. 241, No. 1-4, XP-005254490, Dec. 1, 2005, pp. 753-758.

(Continued)

*Primary Examiner* — Kiho Kim
(74) *Attorney, Agent, or Firm* — Oblon, Spivak, McClelland, Maier & Neustadt, L.L.P.

(57) ABSTRACT

A device which includes a sealed neutron tube, equipped with an alpha particle detector and a gamma radiation detector is placed in a first position. Steps are performed in which neutrons are sent towards an object and in which data provided by the detectors is acquired and processed in order to obtain a three-dimensional mapping of the object. Further, at least one displacement of the device is performed around the object so as to place it in another position, and the steps are repeated wherein, each mapping is geometrically corrected so that it may be updated relative to the set of all mappings, and these mappings are then combined together.

8 Claims, 2 Drawing Sheets

OTHER PUBLICATIONS

G. Perret, et al., "EURITRACK tagged neutron inspection system design", Journal of Physics: Conference Series, Institute of Physics Publishing, vol. 41, No. 1, XP-020110109, May 1, 2006, pp. 375-383.

E. Rhodes, et al., "APSTNG: Neutron Interrogation for Detection of Drugs and Other Contraband", Contraband and Cargo Inspection Technology International Symposium, Oct. 28-30, 1992, 9 pages.

Ed Rhodes, et al., "Advances in Associated-Particle Sealed-Tube Neutron Probe Diagnostics for Substance Detection", Neutron Techniques (Chair Geoffrey Harding) of Conference on Substance Indentification, Analysis, and Technologies for Law Enforcement of European Symposium on Optics for Environmental and Public Safety, Jun. 19-23, 1995, 13 pages.

L. E. Ussery, et al., "Design and Development of the Associated-Particle Three-Dimensional Imaging Technique", LA-12847-MS, UC-706 and UC-700, Oct. 1994, 20 pages.

J. D. L. H. Wood, "A Sealed-Off 14 MeV Neutron Source Incorporating a Solid State Alpha-Particle Detector", Nuclear Instruments and Methods, vol. 21, 1963, pp. 49-52.

* cited by examiner

METHOD OF ANALYSIS OF AN OBJECT BY NEUTRON INTERROGATION, BY THE ASSOCIATED PARTICLE TECHNIQUE, AND DEVICE FOR IMPLEMENTING THE METHOD

TECHNICAL FIELD

The present invention relates to a method for analysing an object by neutron interrogation, by the associated particle technique.

The invention also relates to a device for implementing the method.

It applies in particular to the inspection of abandoned or suspect objects undertaken by intervention teams.

STATE OF THE PRIOR ART

Concerning (1) the associated particle technique, (2) sealed-tube neutron generators, more simply called "sealed neutron tubes", equipped with an alpha particle detector for the implementation of this technique, and (3) associated-particle analysis devices which use such generators, reference is to be made to the following documents:

[1] E. Rhodes and C. W. Peters, "APSTNG: neutron interrogation for detection of drugs and other contraband", Contraband and cargo inspection technology international symposium, 28-30 Oct. 1992, Washington, D.C., USA.

[2] E. Rhodes, C. E. Dickerman and M. Frey, "Advances in associated-particle neutron probe diagnostics for substance detection", Neutron techniques of conference on substance identification, analysis, and technologies for law enforcement of European symposium on optics for environmental and public safety, 19-23 Jun. 1995, Munich, Germany.

[3] L. E. Ussery and C. L. Hollas, "Design and development of the associated-particle three-dimensional imaging technique", LA-12847-MS, UC-706 and UC-700, October 1994.

[4] J. D. Wood, "A sealed-off 14 MeV neutron source incorporating a solid state alpha-particle detector", Nuclear Instruments and Methods 21 (1963), pp. 49-52.

[5] WO 2004/064462, Coded target for neutron source, Invention by Philippe Le Tourneur.

[6] FR 2 738 669, Neutron generator tube equipped with an alpha-particle detector, invention by Yves Serge Cluzeau.

[7] U.S. Pat. No. 6,297,507, Sealed tube neutron generator incorporating an internal associated-ALP, invention by Z. Chen et al.

According to a known method for analysing objects by neutron interrogation, by the associated particle technique, a single data acquisition is carried out for a given position of the sealed neutron tube relative to the object.

A three-dimensional mapping of the object is thus obtained. However the portions of the object that are away from the sealed neutron tube produce less clear portions on the three-dimensional mapping.

PRESENTATION OF THE INVENTION

The purpose of the present invention is, in particular, to remedy this drawback.

It provides better information on an analysed object, by combining information obtained during several acquisition steps carried out at different positions of the sealed neutron tube around the object.

In precise terms the present invention relates to a method for analysing an object by neutron interrogation, by the associated particle technique, wherein
 a device is used which includes a sealed-tube neutron generator equipped with an alpha-particle detector and at least one gamma radiation detector, where the alpha particle detector allows the neutrons emitted by the generator in a given solid angle to be monitored by detecting alpha particles associated with the neutrons emitted, where the gamma radiation detector allows gamma radiation emitted by the object to be detected when the object is placed in the given solid angle and receives the emitted neutrons, and
 the device is placed in a given position relative to the object, where the latter is placed in the given solid angle,
where the method includes steps which involve:
 sending neutrons from the generator towards the object,
 carrying out acquisition of the data which are then provided by the alpha particle detector and gamma radiation detector, and
 processing the data thus acquired in order to obtain a three-dimensional mapping of the object.
where this method is characterised in that
at least one movement of the device is made around the object, in order to place the device in another given position in relation to the object, where the latter is kept fixed in the given solid angle,
 the steps are repeated,
 each three-dimensional mapping is geometrically corrected in order to allow this three-dimensional mapping to be updated relative to the set of all the three-dimensional mappings, and
 the three-dimensional mappings are combined with each other in order to obtain a unique three-dimensional mapping.

According to one specific embodiment of the invention, more than one movement of the device is made around the object in order to obtain more than two three-dimensional mappings of the object.

According to a first specific embodiment of the method which is the subject of the invention, successive positions of the device are determined relative to an absolute reference frame.

According to a second specific embodiment, successive positions of the device are determined relative to each other.

The present invention also relates to a device for implementing the method which is a subject of the invention, where this device includes a sealed-tube neutron generator equipped with an alpha-particle detector and at least one gamma radiation detector, where the alpha particle detector allows the neutrons emitted in a given solid angle to be monitored by detecting alpha particles associated with the neutrons emitted, where the gamma radiation detector allows the gamma radiation emitted by the object to be detected, when the object is placed in the given solid angle and receives the emitted neutrons,
 wherein the device is equipped with:
 means for determining the successive positions of the sealed tube neutron generator relative to an absolute reference frame or in relation to each other, and
 electronic means of processing, suitable for processing data provided by the alpha particle detector and by the gamma radiation detector, for determining the three-dimensional mappings and updating and combining the latter together.

The means for determining the successive positions of the generator may include a displacement sensor.

And the device may furthermore include a mobile machine whereupon the sealed tube neutron generator and the means for determining the successive positions of the latter are mounted.

BRIEF DESCRIPTION OF DRAWINGS

The present invention will be better understood by reading the description of embodiment examples given hereafter, which are purely for indication purposes only and which are in no way restrictive, whilst referring to the appended drawings wherein.

DETAILED PRESENTATION OF SPECIFIC EMBODIMENTS

Figure 1:
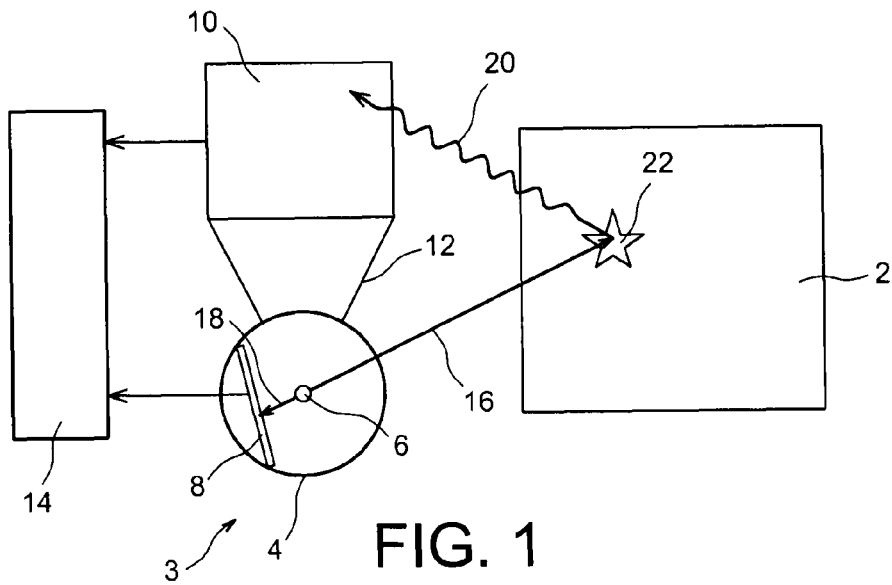
FIG. 1 is a schematic view of a known device, used to implement the associated particle technique.

FIG. 1 is a schematic view of a known device 3, used to implement the associated particle technique in order to analyse an object 2.

This device 3 includes a sealed neutron tube 4 which includes a target 6 and which is equipped with an alpha particle detector 8, more simply called "alpha detector".

The device also includes one gamma detector 10 (but there could be several of these), shielding 12, which protects this gamma detector 10 from emissions from the neutron tube 4, and means 14 for acquiring the data supplied by the detectors 8 and 10, processing the acquired data and obtaining a three-dimensional mapping of the object (where the means 14 are equipped with means of display which are not shown).

The target 6 of the tube 4 is the location of the nuclear reaction $D+T \rightarrow \alpha+n$ (D: deuterium; T: tritium; $\alpha$: alpha particle; n: neutron). Thus there is an alpha particle which follows a trajectory 18 at 180° to the trajectory 16 followed by a neutron emitted towards the object 2.

The detection of the alpha particle associated with the neutron by the detector 8 allows the trajectory 16 of the neutron to be known.

If a gamma photon 20 from the interaction of this neutron and an unknown atom 22 of the object is detected, the energy of the gamma photon makes it possible to identify the nature of the atom. Furthermore, the time difference between the detection of the alpha particle and the detection of the gamma photon, and knowledge of the respective speeds of the alpha particle, of the neutron and of the gamma photon also make it possible to know where the atom 22 is located within the object 2.

At the end of data acquisition and data processing, the object is known through the nature of its atoms and the location of these. A three-dimensional mapping of the object is thus obtained.

Let us now turn to an example of the method which is the subject of the invention and that will now be described with reference to FIG. 2.

This method makes it possible to analyse an object 24 by neutron interrogation by the associated particle technique. In its implementation the method uses a device 26 of the type which has been described with reference to FIG. 1.

This device 26 therefore includes a sealed tube neutron generator (not shown), equipped with an alpha particle detector (not shown) and at least one gamma radiation detector (not shown).

The alpha particle detector makes it possible to monitor the neutrons emitted by the generator in a given solid angle, by detecting the alpha particles associated with the neutrons emitted. As for the gamma radiation detector, this makes it possible to detect gamma radiation emitted by the object 24 when the latter is placed in the given solid angle and receives the emitted neutrons.

According to the invention, the device 26 is placed in a given position P1 relative to the object 24, where the latter is placed in the given solid angle.

Then the following steps are carried out:
- neutrons are sent from the generator towards the object 24,
- data is acquired which is then provided (in the form of electrical signals) by the alpha particle detector and the gamma radiation detector, and
- the data thus acquired is processed in order to obtain a three-dimensional mapping of the object 24.

According to the invention, one displacement or several successive displacements of the device 26 are then made around the object 24, in order to place this device 26 in another given position, or successively in several other given positions, in relation to the object, where the latter is kept fixed and always located in the given solid angle.

In the example under consideration, three successive displacements are made, so that the device 26 successively occupies positions P2, P3 and P4 after it has occupied position P1.

For each of these positions:
- each three-dimensional mapping obtained is geometrically corrected in order to allow this three-dimensional mapping to be updated relative to the set of all three-dimensional mappings, and
- the three-dimensional mappings are combined with each other in order to obtain a unique three-dimensional mapping.

We will return to these aspects of the invention later.

In order to implement the method the device 26 is equipped with:
- means 28 for determining its successive positions P1 to P4 (n other words, the successive positions of the sealed tube neutron generator), and
- electronic means of processing 30 which make it possible not only to acquire and to process data supplied by the alpha particle detector and by the gamma radiation detector and to determine the three-dimensional mappings as with the means 14 in FIG. 1, but also make it possible to update the three-dimensional mappings, using the set positions, and to combine these mappings together.

It should be specified that the means 28 are provided to determine the successive positions of the neutron generator either in relation to an absolute reference frame R, or in relation to each other. In order to do this, in the example the means 28 are made up of a displacement sensor, for example of the inertial unit type.

Furthermore the device 26 may quite simply be a portable device. It may, however, also be fitted to a mobile machine.

Figure 2:
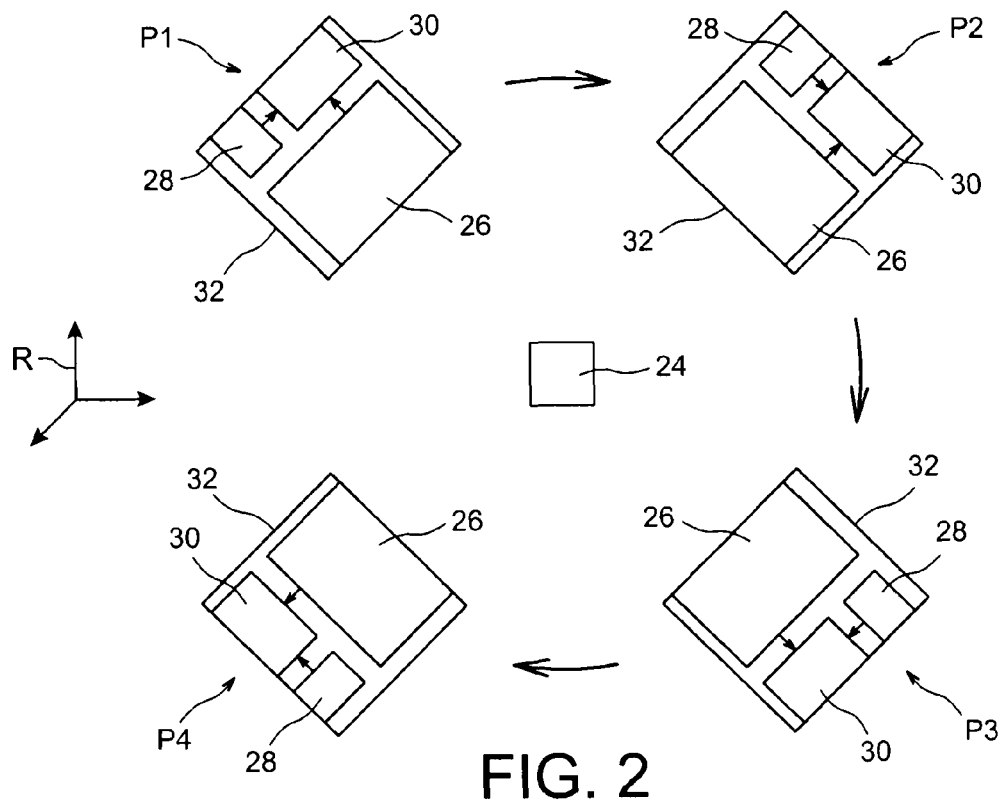
FIG. 2 is a schematic illustration of a specific embodiment of the device which is the subject of the invention.

In FIG. 2 such a mobile machine can be seen whereupon are fitted the device 26 and the displacement sensor 30 which enable the successive positions of the device to be determined.

Let us now return to the associated particle technique and its use in the invention.

As has been seen, this technique is implemented through the use of a sealed neutron tube which uses the deuterium-tritium fusion reaction to produce neutrons and which is equipped with an alpha particle detector making it possible to monitor the neutrons emitted in a certain solid angle.

The principle behind the analysis of the object involves sending neutrons towards it and collecting the gamma radiation returning. By means of a coincidence technique between the gamma radiation and the alpha particles which are, as it were, attached to the start and to the end of the neutron trajectory, a spatial component is added to the information obtained (which is the nature of the material of which the object is formed).

The final result is a three-dimensional mapping of the object. Each elementary volume of the latter is described by the nature of the material (carbon, oxygen, nitrogen, iron, silicon etc.) and by the amount of this material that the volume contains. By extension, it is customary to call the grid that makes up the mapping an "image in three dimensions" of the object.

As has been seen, this three-dimensional grid is acquired by positioning the instrument or device close to the object (position called p1) and by carrying out a data acquisition (neutron emission and collection of gamma radiation emitted from the object).

If the instrument is displaced around the object (which remains fixed) so that this instrument is placed in a new position p2 in accordance with the invention, a new description of the object can be acquired in a new three-dimensional grid which cannot be superimposed on the preceding one in the state as it exists.

The aim of the invention is to allow these two grids to be combined. The basis for this combination is an understanding of the geometric displacement (translation and rotation) which is carried out during the passage of the instrument from the first position p1 to the second position p2.

Figure 3:
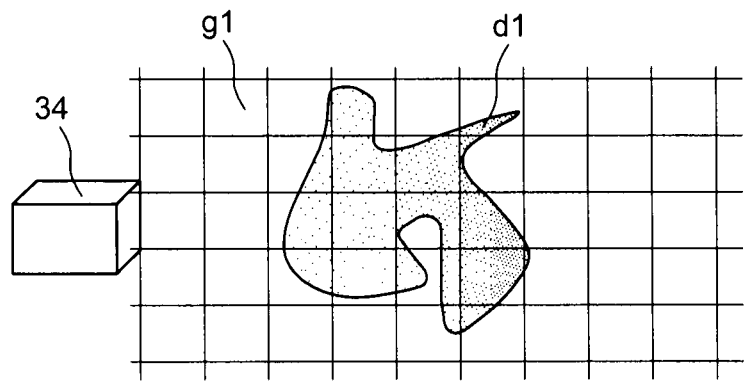
FIGS. 3 to 5 are schematic illustrations of a specific embodiment of the method which is the subject of the invention.
Figure 4:
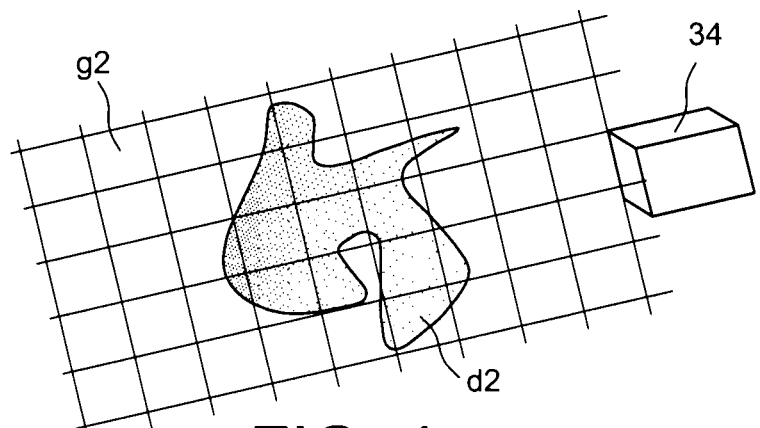
Figure 5:
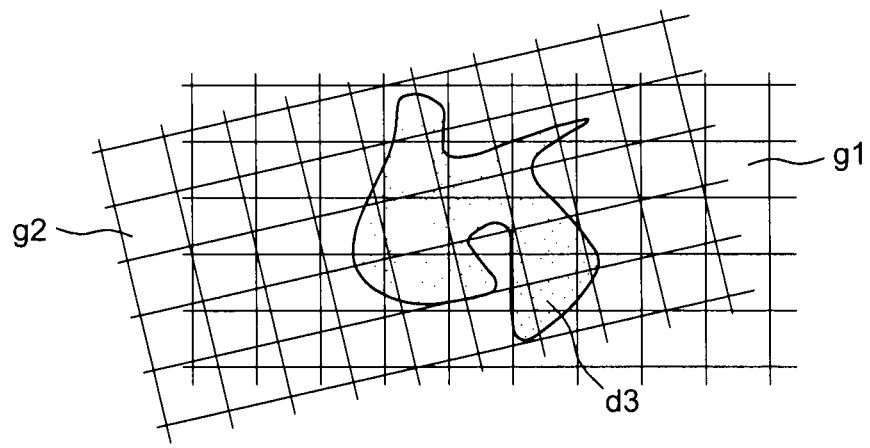

This is illustrated schematically by FIGS. 3 to 5. These show the grid g1 obtained for the position p1 of the instrument 34 (FIG. 3), as well as the description d1 of the object in this grid g1.

Similarly grid g2, obtained for the position p2 of the instrument 34 (FIG. 4) is shown, as well as the description d2 of the object in this grid g2.

It should be recalled that the object has not moved between the two acquisitions which result, respectively, in grids g1 and g2: only the instrument has been displaced.

In FIGS. 3 and 4 the portions of the object which are away from the instrument are shown as being darker than the rest of the object, symbolising the fact that these portions are less clearly visible.

In accordance with the invention, the results of the two acquisitions (FIGS. 3 and 4) are summed together thanks to knowledge of the displacement of the instrument between these two acquisitions. The result is presented in FIG. 5. This figure symbolically represents the fact that the object is now well-known: its description d3 no longer has any dark portions.

The benefit of the invention rests in the fact that it makes it possible to obtain a good view of the object by multiplying the points of view and by making them coherent in a single final view.

In security applications where the neutron instrument is portable and makes it possible to verify the contents of abandoned packages or baggage, three or four successive positions of the instrument around the object may be useful.

In another use for the invention, the neutron instrument is on-board a mobile machine such as, for example, a robot. Each acquisition may be compared to a sort of photograph which contributes to a final image of the object, where the various photographs are incorporated in the final image after geometrical indexing, that is, each elementary acquisition, naturally referenced in relation to the instrument, is also geometrically referenced in relation to the object that is inspected, and then these acquisitions are summed together after being updated in a common geometrical reference frame.

This geometrical indexing may be carried out by referencing of the position of the instrument during each elementary acquisition.

As has been seen, the invention requires that various images be combined together, that is, that the images are updated relative to each other, with the geometrical reference frame of each being taken into consideration.

In order to do this, one needs:
knowledge of the successive positions of the instrument referred to relative to an absolute reference frame or a knowledge of these successive positions relative to each other and
to geometrically correct each acquisition, relative to the analysed scene (the object) and not relative to the instrument, so as to be able to update this acquisition relative to the set of all acquisitions.

The geometrical correction of each acquisition may be achieved by transfer of the positions of atoms identified in the geometric reference frame of the instrument towards the geometric reference frame of the object being analysed.

The updating of this acquisition may be achieved by the addition of images of common geometric reference frame.

The invention may therefore be implemented using a neutron instrument whose various positions in a given geometric reference frame can be manually identified, or using a neutron instrument which is equipped with a displacement sensor that is capable of operating in real time. The instrument software carries out the calculations necessary for the updates of the elementary images.

A neutron instrument is therefore available which is portable, or on-board a robot, and which is equipped with a neutron tube in order to implement the associated particle technique. This instrument is equipped with a displacement sensor (inertial unit) which makes it possible to index the acquisitions carried out and it is equipped with a software which makes it possible to update and to combine together the various acquisitions.

Alternatively, the geometric indexing of acquisitions is carried out by a manual method and the instrument is once more equipped with a software which makes it possible to update and combine together the various acquisitions.

The invention claimed is:

1. A method for analysing an object by neutron interrogation, by the associated particle technique, wherein a device is used which includes a sealed-tube neutron generator equipped with an alpha-particle detector and at least one gamma radiation detector, where the alpha particle detector allows neutrons emitted by the generator in a given solid angle to be monitored by detecting alpha particles associated with the neutrons emitted, where the gamma radiation detector allows gamma radiation emitted by the object to be detected when the object is placed in the given solid angle and receives the emitted neutrons, and the device is placed in a given position relative to the object, where the object is placed in the given solid angle, the method comprising:
sending neutrons from the generator towards the object;
carrying out acquisition of the data which is then provided by the alpha particle detector and gamma radiation detector;
processing the data thus acquired in order to obtain a three-dimensional mapping of the object;
performing at least one displacement of the device around the object, in order to place the device in another given position in relation to the object, where the object is kept fixed in the given solid angle;

repeating the sending, carrying and processing steps for the other position of the device;

correcting each three-dimensional mapping geometrically in order to allow the mapping to be updated relative to a set of all the three-dimensional mappings; and combining the three-dimensional mappings with each other in order to obtain a single three-dimensional mapping.

2. The method according to claim 1, wherein more than one displacement of the device is made around the object so as to obtain more than two three-dimensional mappings of the object.

3. The method according to claim 1, wherein the successive positions of the device are determined relative to an absolute reference frame.

4. The method according to claim 1, wherein the successive positions of the device are determined relative to each other.

5. A device comprising:

a sealed-tube neutron generator equipped with an alpha-particle detector and at least one gamma radiation detector, where the alpha particle detector allows the neutrons emitted by the generator in a given solid angle to be monitored by detecting alpha particles associated with the neutrons emitted, where the gamma radiation detector allows gamma radiation emitted by the object to be detected when the object is placed in the given solid angle and receives the emitted neutrons;

means for determining successive positions of the sealed-tube neutron generator relative to an absolute reference frame or relative to each other; and electronic means of processing data provided by the alpha particle detector and by the gamma radiation detector, for determining three-dimensional mappings of the object, and for updating and combining together the three-dimensional mappings.

6. The device according to claim 5, wherein the means for determining the successive positions of the generator include a displacement sensor.

7. The device according to claim 5, further comprising a mobile machine whereupon the sealed tube neutron generator and the means for determining the successive positions of the sealed tube neutron generator are mounted.

8. A non-transitory computer readable medium having stored thereon a program that when executed by a computer causes the computer to execute a method comprising:

sending neutrons from a generator towards an object;

carrying out acquisition of data provided by an alpha particle detector and a gamma radiation detector;

processing the acquired data to obtain a three-dimensional mapping of the object;

performing at least one displacement of a device around the object, to place the device in another given position in relation to the object, wherein the object is kept fixed in a given solid angle;

repeating the sending, carrying and processing steps for the other position of the device;

correcting each three-dimensional mapping geometrically in order to allow the mapping to be updated relative to a set of all the three-dimensional mappings; and combining the three-dimensional mappings with each other in order to obtain a single three-dimensional mapping.

* * * * *